United States Patent
Hamaguchi et al.

(10) Patent No.: US 9,399,064 B2
(45) Date of Patent: Jul. 26, 2016

(54) PITAVASTATIN-CONTAINING PREPARATION AND METHOD FOR PRODUCING SAME

(75) Inventors: Nobuko Hamaguchi, Osaka (JP); Shouichi Hosaka, Osaka (JP); Kenji Nozawa, Osaka (JP); Yasufumi Okamura, Osaka (JP)

(73) Assignee: SAWAI PHARMACEUTICAL CO., LTD., Osaka (JP)

( * ) Notice: Subject to any disclaimer, the term of this patent is extended or adjusted under 35 U.S.C. 154(b) by 202 days.

(21) Appl. No.: 14/111,459

(22) PCT Filed: Apr. 10, 2012

(86) PCT No.: PCT/JP2012/059745
§ 371 (c)(1),
(2), (4) Date: Oct. 11, 2013

(87) PCT Pub. No.: WO2012/141160
PCT Pub. Date: Oct. 18, 2012

(65) Prior Publication Data
US 2014/0031390 A1 Jan. 30, 2014

(30) Foreign Application Priority Data
Apr. 12, 2011 (JP) ................................. 2011-088236

(51) Int. Cl.
*A01N 43/42* (2006.01)
*A61K 31/47* (2006.01)
*A61K 47/02* (2006.01)
*A61K 9/20* (2006.01)

(52) U.S. Cl.
CPC .............. *A61K 47/02* (2013.01); *A61K 9/2009* (2013.01); *A61K 31/47* (2013.01)

(58) Field of Classification Search
None
See application file for complete search history.

(56) References Cited

U.S. PATENT DOCUMENTS

| | | | |
|---|---|---|---|
| 5,030,447 | A | 7/1991 | Joshi et al. |
| 5,356,896 | A | 10/1994 | Kabadi et al. |
| 6,123,971 | A | 9/2000 | Tidland |
| 6,680,341 | B1 | 1/2004 | Kerc et al. |
| 2004/0072894 | A1 | 4/2004 | Kerc |
| 2009/0117181 | A1 | 5/2009 | Uehara et al. |

FOREIGN PATENT DOCUMENTS

| | | | | |
|---|---|---|---|---|
| JP | 11-503763 | A | 3/1999 | |
| JP | 2002-532409 | A | 10/2002 | |
| JP | 2003-002829 | A | 1/2003 | |
| JP | 2004-527518 | A | 9/2004 | |
| JP | 2005-035989 | A | 2/2005 | |
| WO | 97/23200 | A1 | 7/1997 | |
| WO | WO 9723200 | A1 * | 7/1997 | ........... A61K 9/2009 |

OTHER PUBLICATIONS

International Search Report of PCT/JP2012/059745 dated May 22, 2012.

* cited by examiner

*Primary Examiner* — Dennis Heyer
*Assistant Examiner* — Daniel M Podgorski
(74) *Attorney, Agent, or Firm* — Sughrue Mion, PLLC

(57) ABSTRACT

The present invention provides: a pitavastatin-containing preparation containing pitavastatin or a pharmacologically acceptable salt thereof and at least one kind of a basic additive selected from the group consisting of basic magnesium compounds and basic calcium compounds, and an aqueous solution or an aqueous dispersion of the pitavastatin-containing preparation having a pH of more than 8 and 10 or less; and a method for producing a pitavastatin-containing preparation, including blending at least one kind of a basic additive selected from the group consisting of basic magnesium compounds and basic calcium compounds with pitavastatin or a pharmacologically acceptable salt thereof, to make an aqueous solution or an aqueous dispersion of the pitavastatin-containing preparation have a pH of more than 8 and 10 or less.

6 Claims, No Drawings

US 9,399,064 B2

PITAVASTATIN-CONTAINING PREPARATION AND METHOD FOR PRODUCING SAME

TECHNICAL FIELD

The present invention relates to a pitavastatin-containing preparation which is useful in treatment of patients with hypercholesterolemia, familial hypercholesterolemia and the like and a method for producing the same.

BACKGROUND ART

Pitavastatin or a salt thereof has activity which specifically and antagonistically inhibits an HMG-CoA reductase which is a rate-controlling enzyme of the biosynthetic pathway of cholesterol and is clinically used in the treatment of hypercholesterolemia, familial hypercholesterolemia and the like on the basis of exhibiting a cholesterol-lowering effect, a triglyceride-lowering effect, inhibitory effect on an arteriosclerosis progression and the like.

However, HMG-CoA reductase inhibitors such as pitavastatin, pravastatin, fluvastatin and atorvastatin have a 7-substituted-3,5-dihydroxy-6-heptenoic acid (or a 7-substituted-3, 5-dihydroxy heptanoic acid) structure, and have problems in that a lactone is produced and stability is poor in a low pH environment. In a case where stability of a drug is poor, there is a possibility that efficacy of the drug is decreased and safety is impaired. Accordingly, it is necessary to stabilize pitavastatin or a salt thereof which is an active ingredient, in a pitavastatin-containing preparation.

As a stabilization method of an HMG-CoA reductase inhibitor-containing preparation, a method of blending a basification agent which gives a pH of 9 or more with an aqueous dispersion of a pravastatin-containing preparation (refer to Patent Literature 1), a method of blending an alkaline medium which can give a pH of at least 8 with an aqueous solution or a dispersion of a fluvastatin-containing preparation (refer to Patent Literature 2), a method of blending a stabilizing metal salt additive with an atorvastatin-containing preparation (refer to Patent Literature 3) and a method of adding a basic substance such that an aqueous solution or a dispersion of a pitavastatin-containing formulation has a pH of 7 or more to 8 or less (refer to Patent Literature 4) are known.

However, in Patent Literatures 1 to 3, there is no specific description for the stabilization of the pitavastatin-containing preparation. Moreover, in Patent Literature 4, the stabilization of the pitavastatin-containing preparation seems to be achieved, but there are also problems in that the stabilization is insufficient, and when a pH is more than 8, the color tone of the outward appearance changes.

As described above, in methods known in the related art, it has not been possible to obtain a preparation with sufficient stability and without the change of the color tone of the outward appearance in the pitavastatin-containing preparation.

CITATION LIST

Patent Literature

Patent Literature 1: U.S. Pat. No. 5,030,447
Patent Literature 2: U.S. Pat. No. 5,356,896
Patent Literature 3: U.S. Pat. No. 6,123,971
Patent Literature 4: WO 97/23200

SUMMARY OF INVENTION

Technical Problem

An object of the present invention is to provide a pitavastatin-containing preparation which can effectively suppress the generation of a lactone from pitavastatin or a pharmacologically acceptable salt thereof in the pitavastatin preparation, is stabilized and hardly has a color change, and a method for producing the same.

Solution to Problem

As a result of having repeated thorough studies in order to achieve the above object, the present inventors found that a pitavastatin-containing preparation which is more stable and hardly has a color change can be obtained by blending at least one kind of a basic additive of a basic substance, particularly, a basic magnesium compound and a basic calcium compound with pitavastatin or a pharmacologically acceptable salt thereof, to make an aqueous solution or an aqueous dispersion of the pitavastatin-containing preparation have a pH of more than 8 and 10 or less. The present inventors have repeatedly conducted further examination based on the knowledge, thereby completing the present invention.

The present invention is to provide a pitavastatin-containing preparation and a method for producing the same as described below.

1. A pitavastatin-containing preparation containing pitavastatin or a pharmacologically acceptable salt thereof and at least one kind of a basic additive selected from the group consisting of basic magnesium compounds and basic calcium compounds, of which an aqueous solution or an aqueous dispersion of the pitavastatin-containing preparation has a pH of more than 8 and 10 or less.

2. The pitavastatin-containing preparation according to Item 1 in which pitavastatin or the pharmacologically acceptable salt thereof is a pitavastatin calcium salt.

3. The pitavastatin-containing preparation according to Item 1 or 2 in which the basic additive is a basic magnesium compound.

4. The pitavastatin-containing preparation according to Item 3 in which the basic magnesium compound is at least one kind selected from the group consisting of magnesium hydroxide, magnesium carbonate, magnesium silicate and magnesium aluminometasilicate.

5. The pitavastatin-containing preparation according to Item 1 or 2 in which the basic additive is a basic calcium compound.

6. The pitavastatin-containing preparation according to Item 5 in which the basic calcium compound is calcium carbonate and/or calcium silicate.

7. The pitavastatin-containing preparation according to Item 5 in which the basic calcium compound is calcium carbonate.

8. The pitavastatin-containing preparation according to any one of Items 1 to 7 in which the content of the basic additive is about 10 parts by weight to 1000 parts by weight relative to 100 parts by weight of pitavastatin or the pharmacologically acceptable salt thereof.

9. The pitavastatin-containing preparation according to any one of Items 1 to 8 in which the pH of the aqueous solution or the aqueous dispersion thereof is about 8.4 to 9.9.

10. A method for producing a pitavastatin-containing preparation in which at least one kind of a basic additive selected from the group consisting of basic magnesium compounds and basic calcium compounds is blended with pitavastatin or a pharmacologically acceptable salt thereof so that an aqueous solution or an aqueous dispersion of the pitavastatin-containing preparation is made to have a pH of more than 8 to 10 or less.

Advantageous Effects of Invention

According to the present invention, significant effects as described below can be obtained by blending at least one kind of a basic additive of a basic magnesium compound and a basic calcium compound with pitavastatin or a pharmacologically acceptable salt thereof, to make an aqueous solution or an aqueous dispersion of the pitavastatin-containing preparation have a pH of more than 8 and 10 or less.

(1) The pitavastatin-containing preparation which effectively suppresses the generation of a lactone of pitavastatin or a pharmacologically acceptable salt thereof in a pitavastatin preparation, is stabilized and hardly has a color change, is obtained.

(2) Since the obtained pitavastatin-containing preparation effectively suppresses the generation of a lactone, is stabilized and hardly has a color change, decrease in a drug efficacy and impairing of safety of pitavastatin or a pharmacologically acceptable salt thereof can be prevented for a long period of time.

(3) The stabilized pitavastatin-containing preparation can be easily manufactured by a simple method in which at least one kind of a basic additive selected from the group consisting of basic magnesium compounds and basic calcium compounds is blended with pitavastatin or a pharmacologically acceptable salt thereof, to make an aqueous solution or an aqueous dispersion of the pitavastatin-containing preparation have a pH of more than 8 and 10 or less.

DESCRIPTION OF EMBODIMENTS

Pitavastatin-Containing Preparation

The pitavastatin-containing preparation of the present invention contains pitavastatin or a pharmacologically acceptable salt thereof and at least one kind of a basic additive selected from the group consisting of basic magnesium compounds and basic calcium compounds, and a pH of an aqueous solution or an aqueous dispersion thereof is more than 8 to 10 or less. And thus, pitavastatin or a pharmacologically acceptable salt thereof is stabilized, and furthermore, the color change of the preparation is suppressed. The pH mentioned herein is a pH value measured at the time when purified water is added to a solid preparation containing pitavastatin or a pharmacologically acceptable salt thereof to form an aqueous solution or an aqueous dispersion of 5% by weight. There is a tendency that the generation of a lactone increases during storage when a pH of an aqueous solution or an aqueous dispersion thereof is equal to or less than 8, and there is a tendency that color change of the preparation easily occurs during storage when a pH is more than 10. Therefore, none of such pH values are preferable. It is preferable that a pH of an aqueous solution or an aqueous dispersion is about 8.4 to 9.9.

The pitavastatin-containing preparation of the present invention is a preparation in which pitavastatin or a pharmacologically acceptable salt thereof, at least one kind of a specific basic additive selected from the group consisting of basic magnesium compounds and basic calcium compounds, various additives which are pharmacologically acceptable and usually used in the pharmaceutical field, for example, a diluent, a disintegrant, a binder and the like are blended and the resultant is contained.

As the pitavastatin-containing preparation, tablets such as an uncoated tablet, a coated tablet, a sustained-release tablet, an orally disintegrating tablet and a chewable tablet; a granule; powder and the like are preferably included.

Pitavastatin

Pitavastatin is an active pharmaceutical ingredient of the preparation of the present invention, and the chemical name thereof is bis{(3R,5S,6E)-7-[2-cyclopropyl-4-(4-fluorophenyl)-3-quinolyl]-3,5-dihydroxy-6-heptenoate}. As described above, pitavastatin has inhibitory activity on HMG-CoA reductase (3-hydroxy-3-methylglutaryl coenzyme A).

As a pharmacologically acceptable salt of pitavastatin, a calcium salt, a magnesium salt, a sodium salt, a potassium salt and the like can be used, in particular, a calcium salt is preferably used.

Specific Basic Additive

The pitavastatin-containing preparation of the present invention is required to contain at least one kind of a basic additive selected from the group consisting of basic magnesium compounds and basic calcium compounds. As a basic magnesium compound, for example, magnesium silicate, magnesium hydroxide, magnesium carbonate, magnesium aluminometasilicate and the like can be exemplified. Furthermore, as a basic calcium compound, for example, calcium silicate, calcium carbonate and the like can be exemplified, and calcium carbonate is preferable. As calcium carbonate, precipitated calcium carbonate can be also used.

The content of a basic additive is the amount at the time when a pH of an aqueous solution or an aqueous dispersion of the pitavastatin-containing preparation is more than 8 to 10 or less, and by this, it is possible to suppress the generation of a lactone and the color change of the preparation during storage. Specifically, the content of a basic additive is preferably about 10 parts by weight to 1000 parts by weight relative to 100 parts by weight of pitavastatin or a pharmacologically acceptable salt thereof.

Additive

Pitavastatin or a pharmacologically acceptable salt thereof and the above-described specific basic additives are usually used in combination with at least one kind of a pharmacologically acceptable additive of a diluent, a disintegrant and a binder.

As a diluent, for example, crystalline cellulose, starch such as corn starch; lactose, powdered sugar, sucrose, glucose, mannitol, light anhydrous silicic acid, talc, xylitol, sorbitol and the like are exemplified. These diluents can be used alone, or two or more kinds thereof can be used in combination.

As a disintegrant, for example, crystalline cellulose, sodium carboxymethyl starch, carmellose, carmellose calcium, carmellose sodium, croscarmellose sodium, cross-linked polyvinyl pyrrolidone, low-substituted hydroxypropylcellulose, starch and the like are exemplified. These disintegrants can be used alone, or two or more kinds thereof can be used in combination.

As a binder, binders in the related art, for example, sucrose, gelatin, powdered gum arabic, methylcellulose, hypromellose, hydroxypropylcellulose, carboxymethylcellulose, crystalline cellulose-carboxymethylcellulose sodium, polyvinyl pyrrolidone, pullulan, dextrin, tragacanth, sodium alginate, pregelatinized starch, polyvinyl alcohol and the like are exemplified. These binders can be used alone, or two or more kinds thereof can be used in combination.

The ratio of at least one kind of an additive among these diluents, disintegrants and binders can be selected from a range of about 100 parts by weight to 12000 parts by weight relative to 100 parts by weight of pitavastatin or a pharmacologically acceptable salt thereof. Normally about 300 parts by weight to 10000 parts by weight is preferable, and about 500 parts by weight to 8000 parts by weight is more preferable.

The pitavastatin-containing preparation may further contain pharmacologically acceptable additives in the related art, for example, a lubricant, a fluidizer, an antistatic agent, a surfactant, a flavoring agent, a wetting agent, a filler, a bulking agent, an adsorbent, a preservative (for example, an antiseptic and the like), a buffering agent, a disintegration extending agent and a colorant other than the pharmacologically acceptable additives such as a diluent, a disintegrant and a binder.

As the above-described lubricant, for example, magnesium stearate, light anhydrous silicic acid, talc, calcium stearate, sodium stearyl fumarate, sucrose esters of fatty acids, L-leucine and the like can be exemplified. As an antistatic agent, for example, light anhydrous silicic acid and the like can be exemplified. As a surfactant, for example, anionic surfactants such as sodium alkylsulphate; non-ionic surfactants such as polyoxyethylene sorbitan fatty acid esters, polyoxyethylene fatty acid esters and polyoxyethylene castor oil derivatives; and the like can be exemplified. As a flavoring agent, for example, sweeteners such as sucrose, lactose, mannitol, xylitol, saccharin, saccharin sodium, aspartame, stevioside, sucralose, acesulfame potassium, thaumatin and erythritol; fragrances; and the like can be exemplified. As a wetting agent, for example, polyethylene glycol (macrogol), glycerin, propylene glycol and the like can be exemplified.

These other additives in the related art can be used alone, or two or more kinds thereof can be used in combination. The contents of these components in the final preparation are not particularly limited.

Method for Producing the Pitavastatin-Containing Preparation

A method for producing the pitavastatin-containing preparation of the present invention is a method in which one or more kinds of basic additives selected from the group consisting of basic magnesium compounds and basic calcium compounds are blended with pitavastatin or a pharmacologically acceptable salt thereof, so that an aqueous solution or an aqueous dispersion thereof is made to have a pH of more than 8 to 10 or less. A pH of an aqueous solution or an aqueous dispersion thereof is preferably about 8.4 to 9.9.

As described above, the blending amount of a basic additive is the amount at the time when a pH of an aqueous solution or an aqueous dispersion of the obtained pitavastatin-containing preparation is more than 8 to 10 or less. Specifically, the content of a basic additive is preferably about 10 parts by weight to 1000 parts by weight relative to 100 parts by weight of pitavastatin or a pharmacologically acceptable salt thereof.

In a case where the preparation containing pitavastatin or a salt thereof and a basic additive is a tablet, the tablet can be manufactured according to well-known methods in the pharmaceutical field. For example, tablets can be manufactured by performing respective operations such as blending, granulating, drying, regulating particle size and tableting with respect to pitavastatin or a salt thereof, a specific basic additive and additives such as a diluent, a disintegrant and a binder using solvent usually used according to well-known methods in the related field. After regulating particle size and before tableting, a disintegrant, a lubricant and the like may be blended. Among these operations, a granulation operation may be performed using an apparatus, for example, an agitation granulator, a fluidized-bed granulator, a brabender, a biaxial granulator and the like. Furthermore, tableting can be performed using a commercially available tableting machine. Preparations other than tablet, for example, granule, powder or the like can be also manufactured according to well-known methods in the pharmaceutical field.

In manufacture of pitavastatin-containing tablets of the present invention, coating may be performed with respect to uncoated tablets or uncoated granules after granulating. In a case of coating, the coating may be preferably performed by using a film coating machine, a fluidized-bed granulator or the like. In the coating, well-known coating agents in the related art such as hypromellose, hydroxypropylcellulose, methylcellulose, polyvinyl alcohol, polyvinyl pyrrolidone, polyethylene glycol, hydroxypropylmethylcellulose acetate succinate, hypromellose phthalate, cellulose acetate phthalate, aminoalkyl methacrylate copolymer E, aminoalkyl methacrylate copolymer RS, methacrylic acid copolymer L, methacrylic acid copolymer LD, methacrylic acid copolymer S, dried methacrylic acid copolymer LD, ethyl acrylate-methyl methacrylate copolymer dispersion and sucrose can be used.

In a case where the pitavastatin-containing preparation of the present invention is used, an effective amount for a treatment of disease such as hypercholesterolemia or familial hypercholesterolemia may be administered to human. The dosage may vary according to a patient's age, body weight, symptom, gender and the like, however, for example, normally, about 0.5 mg to 50 mg as pitavastatin or a pharmacologically acceptable salt thereof can be orally administered once per day, or if necessary; several times per day.

The pitavastatin-containing preparation of the present invention has high stability. For example, after storing for 7 days under a non-packing opening condition at 60° C. and 60% RH, the generation of a lactone is extremely small and a color change of the preparation is hardly observed.

The pitavastatin-containing preparation of the present invention may be PTP-packed or bottle-packed (example: a plastic bottle, a glass bottle, an aluminum can). Furthermore, these packed preparations may be further secondary packaged by a pillow-package and the like. A deodorant, a desiccant, a deoxygenating agent and the like may be included together in the package.

EXAMPLES

Hereinafter, the present invention will be described in more detail with reference to examples and comparative examples, but the present invention is not limited to these examples in any way.

Example 1

After mixing 1.0 g of a pitavastatin calcium salt, 66.4 g of lactose hydrate, 8.0 g of low-substituted hydroxypropylcellulose and 2.4 g of magnesium hydroxide by a mortar, a hypromellose aqueous solution (solid content is 1.4 g) was added thereto and granulation was performed by a wet kneading method. The obtained granulated material was dried and particle size was regulated to obtain regulated material. 0.8 g of magnesium stearate was added to the obtained particle-size regulated material to mix. The obtained mixture was tableted using a single punch tableting machine with φ6R surface punch such that the weight of one tablet is 80 mg and the thickness is 2.8 mm. Thus, pitavastatin-containing tablets of the present invention were obtained.

The formulation per one uncoated tablet is as follows:

| | |
|---|---|
| Pitavastatin calcium salt | 1.0 mg |
| Lactose hydrate | 66.4 mg |
| Low-substituted hydroxypropylcellulose | 8.0 mg |
| Magnesium hydroxide | 2.4 mg |
| Hypromellose | 1.4 mg |
| Magnesium stearate | 0.8 mg |

Examples 2 to 7

Respective pitavastatin-containing tablets of the present invention having the weight 80 mg and the thickness of 2.8 mm per tablet were obtained in the same manner as Example 1 except that 2.4 g of magnesium carbonate (Example 2), 2.4 g of magnesium aluminometasilicate (Example 3), 2.4 g of calcium carbonate (Example 4), 2.4 g of precipitated calcium carbonate (Example 5), 2.4 g of magnesium silicate (Example 6) or 2.4 g of calcium silicate (Example 7) were used instead of 2.4 g of magnesium hydroxide in Example 1.

Comparative Examples 1 to 7

For comparison, respective pitavastatin-containing tablets of the present invention having the weight of 80 mg and the thickness of 2.8 mm per tablet were obtained in the same manner as Example 1 except that 2.4 g of magnesium oxide (Comparative Example 1), 2.4 g of calcium oxide (Comparative Example 2), 2.4 g of calcium chloride (Comparative Example 3), 2.4 g of magnesium sulfate (Comparative Example 4), 2.4 g of sodium sulfate (Comparative Example 5), 2.4 g of disodium hydrogen phosphate (Comparative Example 6) or 2.4 g of trisodium phosphate (Comparative Example 7) were used instead of 2.4 g of magnesium hydroxide in Example 1.

A pH of an aqueous dispersion was measured with respect to respective tablets obtained from the above-described Examples 1 to 7 and Comparative Examples 1 to 7 and a stability test was performed. A pH measurement method and a stability test method were as follows.

pH Measurement Method

Two pitavastatin-containing tablets were added to 3.2 mL of purified water and the resultant was shaken to obtain a 5 wt % aqueous dispersion of the tablets. A pH of the aqueous dispersion was measured using a pH meter.

Stability Test Method

A stability test was performed by storing the pitavastatin-containing tablet for 7 days under the non-packing open condition at 60° C. and 60% RH. After the test, the generated amount of a lactone was measured by HPLC. In addition, a color change was visually observed with respect to tablets at the beginning of the test and at the end of the test.

The generated amount of a lactone was calculated as the ratio (%) of a peak area of a lactone with respect to a peak area of pitavastatin from the HPLC measurement result. The HPLC measurement method was as follows.

HPLC Measurement Method

Detector: ultraviolet absorption photometer (measurement wavelength: 245 nm)
Column: octylsilyl silica gel
Column temperature: constant temperature near 40° C.
Mobile phase: a mixture of a mobile phase A which is 0.05 mol/L ammonium acetate solution and a mobile phase B formed of methanol-acetonitrile-tetrahydrofuran
Flow rate: 1.25 mL/min Table 1 shows the kinds of basic additives, the pH of an aqueous dispersion of tablets and the stability test result (generated amount of a lactone and a color change) of Examples 1 to 7 and Comparative Examples 1 to 7.

TABLE 1

| | Basic additive | pH | Generated amount of a lactone (%) | Color change |
|---|---|---|---|---|
| Example 1 | Magnesium hydroxide | 9.84 | 0.21 | Unchanged |
| Example 2 | Magnesium carbonate | 9.77 | 0.28 | Unchanged |
| Example 3 | Magnesium aluminometasilicate | 8.55 | 0.36 | Unchanged |
| Example 4 | Calcium carbonate | 8.52 | 0.43 | Unchanged |
| Example 5 | Precipitated calcium carbonate | 8.99 | 0.45 | Unchanged |
| Example 6 | Magnesium silicate | 9.13 | 0.46 | Unchanged |
| Example 7 | Calcium silicate | 9.69 | 0.11 | Changed to thin brown |
| Comparative Example 1 | Magnesium oxide | 10.76 | 0.03 | Changed to yellow |
| Comparative Example 2 | Calcium oxide | 11.58 | 0.36 | Changed to dark brown |
| Comparative Example 3 | Calcium chloride | 6.57 | 1.14 | Unchanged |
| Comparative Example 4 | Magnesium sulfate | 7.12 | 1.48 | Unchanged |
| Comparative Example 5 | Sodium sulfate | 7.09 | 3.92 | Unchanged |
| Comparative Example 6 | Disodium hydrogen sulfate | 8.45 | 8.08 | Unchanged |
| Comparative Example 7 | Trisodium sulfate | 10.22 | 3.52 | Changed to pale yellow |

Table 1 shows that when the pitavastatin-containing preparation has at least one kind of a basic additive selected from the group consisting of basic magnesium compounds and basic calcium compounds, and a pH of an aqueous dispersion thereof is more than 8 to 10 or less, the generation of a lactone is extremely small and a color change was not observed (Examples 1 to 6). On the other hand, in a case of containing a basic sodium compound as an additive, even if a pH is more than 8, the generated amount of a lactone is extremely large (Comparative Examples 6 and 7). Furthermore, in a case where a pH of an aqueous dispersion is equal to 8 or less, the generation of a lactone is large (Comparative Examples 3 to 5), and in a case where a pH is more than 10, a color change was observed (Comparative Examples 1, 2 and 7). In addition, since, in a case of containing calcium silicate as an additive in basic calcium compound (Example 7), a color change was slightly observed, it is more desirable to use calcium carbonate (Examples 4 and 5).

INDUSTRIAL APPLICABILITY

The pitavastatin-containing preparation of the present invention is useful in treatment of patients with hypercholesterolemia, familial hypercholesterolemia and the like and the present invention is effectively used in the pharmaceutical field.

The invention claimed is:

1. A pitavastatin-containing preparation comprising pitavastatin or a pharmacologically acceptable salt thereof and at least one kind of basic additive selected from the group consisting of magnesium hydroxide, magnesium carbonate, and magnesium silicate, wherein an aqueous solution or an aqueous dispersion of the pitavastatin-containing preparation has a pH of more than 8 and 10 or less.

2. The pitavastatin-containing preparation according to claim 1, wherein pitavastatin or the pharmacologically acceptable salt thereof is a pitavastatin calcium salt.

3. The pitavastatin-containing preparation according to claim 1, wherein the basic additive is magnesium carbonate.

4. The pitavastatin-containing preparation according to claim 1, wherein the content of the basic additive is 10 parts by weight to 1000 parts by weight relative to 100 parts by weight of pitavastatin or the pharmacologically acceptable salt thereof.

5. The pitavastatin-containing preparation according to claim 1, wherein the pH of the aqueous solution or the aqueous dispersion thereof is 8.4 to 9.9.

6. A method for producing the pitavastatin-containing preparation according to claim 1, comprising blending at least one kind of a basic additive selected from the group consisting of magnesium hydroxide, magnesium carbonate, and magnesium silicate with pitavastatin or a pharmacologically acceptable salt thereof, wherein an aqueous solution or an aqueous dispersion of said preparation has a pH of more than 8 and 10 or less.

* * * * *